(12) United States Patent
Gyakushi et al.

(10) Patent No.: US 12,133,778 B2
(45) Date of Patent: Nov. 5, 2024

(54) CURABLE COMPOSITION FOR DENTURE BASE

(71) Applicant: TOKUYAMA DENTAL CORPORATION, Tokyo (JP)

(72) Inventors: Ayumu Gyakushi, Tokyo (JP); Tatsuya Yamazaki, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 773 days.

(21) Appl. No.: 17/422,504

(22) PCT Filed: Dec. 24, 2019

(86) PCT No.: PCT/JP2019/050723
§ 371 (c)(1),
(2) Date: Jul. 13, 2021

(87) PCT Pub. No.: WO2020/149121
PCT Pub. Date: Jul. 23, 2020

(65) Prior Publication Data
US 2022/0087795 A1 Mar. 24, 2022

(30) Foreign Application Priority Data

Jan. 16, 2019 (JP) ................. 2019-004801

(51) Int. Cl.
| | | |
|---|---|---|
| *A61C 13/01* | (2006.01) | |
| *A61C 8/00* | (2006.01) | |
| *C08L 33/04* | (2006.01) | |

(52) U.S. Cl.
CPC ............ *A61C 13/01* (2013.01); *A61C 8/0016* (2013.01); *C08L 33/04* (2013.01)

(58) Field of Classification Search
CPC .......... A61K 6/35; A61K 6/884; A61K 6/887; C08L 33/04–16; A61C 13/01
See application file for complete search history.

(56) References Cited

U.S. PATENT DOCUMENTS

| | | |
|---|---|---|
| 2002/0065338 A1 | 5/2002 | Shinozaki et al. |
| 2004/0048948 A1 | 3/2004 | Yamashita et al. |
| 2019/0038515 A1 | 2/2019 | Yamagawa et al. |
| 2019/0290551 A1* | 9/2019 | Yamamoto ............. A61K 6/887 |

FOREIGN PATENT DOCUMENTS

| | | |
|---|---|---|
| GB | 2347679 A | 9/2000 |
| JP | H04042364 B2 | 7/1992 |
| JP | H05163113 A | 6/1993 |
| JP | H11335222 A | 12/1999 |
| JP | 2000175941 A | 6/2000 |
| JP | 2000254152 A | 9/2000 |
| JP | 2002104912 A | 4/2002 |
| JP | 2004203773 A | 7/2004 |
| JP | 2009179612 A | 8/2009 |
| JP | 2010018565 A | 1/2010 |
| JP | 2013087076 A | 5/2013 |
| WO | 2002045660 A1 | 6/2002 |
| WO | 2017073664 A1 | 5/2017 |

OTHER PUBLICATIONS

International Search Report issued in corresponding PCT/JP2019/050723; mailed Mar. 24, 2020 (2 pages).
Written Opinion of the International Searching Authority issued in corresponding International Application No. PCT/JP2019/050723; dated Mar. 24, 2020 (3 pages).

* cited by examiner

*Primary Examiner* — Kregg T Brooks
(74) *Attorney, Agent, or Firm* — Osha Bergman Watanabe & Burton LLP

(57) ABSTRACT

A curable composition for a denture base is provided which comprises a paste-like composition containing (A) (meth) acrylic monomers, (B) a monomer-absorbing porous organic cross-linked polymer which can absorb the (A) (meth) acrylic monomers, and (C) a polymerization initiator selected from a photopolymerization initiator and a thermal polymerization initiator, wherein the content of (B) the monomer-absorbing porous organic cross-linked polymer is 20-80 parts by mass per 100 parts by mass of the (A) (meth)acrylic monomers, and the absorption amount: $R_{Ab} = \{(g-A)/(g-B)\}$, measured in accordance with JIS K5101-13-1:2004, and defined by the amount of (A) (meth)acrylic monomers: g-A (unit: g) absorbed per unit amount of (B) the monomer-absorbing porous organic cross-linked polymer: g-B (unit: g) is greater than or equal to 1.5.

7 Claims, No Drawings

CURABLE COMPOSITION FOR DENTURE BASE

TECHNICAL FIELD

The present invention relates to a denture base curable composition, more particularly, to a one-paste type denture base curable composition that can be used as a denture base resin, a denture base hard relining material, a denture base repairing resin, etc.

BACKGROUND ART

The denture base curable composition is a composition used for manufacturing or repairing a denture base. As materials utilizing the composition, a denture base resin used in the production of a new denture base; a denture base hard relining material used when reforming a plate denture that has become poorly fitting in the oral mucosa of a patient due to prolonged use; a denture base repairing resin that is used in lining or reforming a denture base, or in repairing a broken plate denture are known.

As the denture base curable composition, a curable composition including a polymerizable monomer such as methyl methacrylate, etc.; a (meth)acrylic polymer such as polymethylmethacrylate, polyethylmethacrylate, etc.; and a polymerization initiator is commonly used. As the polymerization initiator, a chemical (redox) polymerization initiator, a photo-polymerization initiator, a thermal polymerization initiator, or a combination thereof is used. The denture base curable composition is provided in different forms depending on the type of the polymerization initiator to be used.

For example, in a case in which a chemical polymerization initiator containing a combination of an oxidizing agent (also referred to as a "radical initiator") and a reducing agent (also referred to as a "polymerization accelerator") is used as the polymerization initiator, since the oxidizing agent and the reducing agent can react immediately when they are brought in contact with each other, the denture base curable composition needs to be stored in two or more portions (packaged in two or more portions). In such case, the denture base curable composition is typically provided as a powder-liquid type (for example, see Patent Documents 1 and 2) composed of a liquid agent including a polymerizable monomer and a reducing agent as main components and a powder agent including a (meth)acrylic polymer and an oxidizing agent as main components, or a two-paste type (for example, see Patent Document 3) obtained by formulating a polymerizable monomer and a (meth)acrylic polymer with an oxidizing agent and a reducing agent, respectively, to form pastes.

On the other hand, in a case in which a thermal polymerization initiator and/or a photo-polymerization initiator is used as the polymerization initiator, it is not particularly necessary to package the denture base curable composition in two or more portions, and therefore, it is possible to use as one-paste type.

Patent Document 4 discloses "a denture base resin material, characterized by comprising a mixture of (A) a polymerizable monomer having at least one unsaturated double bond, (B) at least one type of polymer selected from an alkyl (meth) acrylate homopolymer, an alkyl (meth) acrylate copolymer, and a copolymer of an alkyl (meth) acrylate and styrene, and (C) a thermal polymerization catalyst and/or a photo-polymerization catalyst, with at least a part of the component (B) being dissolved in the component (A)".

Further, according to Patent Document 4, the one-paste type denture base resin material is considered to have the following features: (1) the one-paste type denture base resin material does not require bothersome operations of metering and kneading, since kneading the liquid agent and the powder agent or the two types of pastes at the time of use is unnecessary, unlike the denture base resin material of the powder-liquid type or the two-paste type; (2) the one-paste type denture base resin material is in a paste state having a doughy viscosity in advance, and can be immediately used in the production or lining operation of denture base; (3) the one-paste type denture base resin material has extremely excellent operability, because doughy state is maintained until heat or light is applied and has no odor and causes no irritation; (4) the one-paste type denture base resin material after curing has a large elastic energy, an appropriate hardness, and viscous strength, and is unlikely to be easily broken by an impact or a stress; and (5) the one-paste type denture base resin material is unlikely to be stained or discolored due to mixing of bubbles, etc., even if it is used for a long period of time.

Patent Document 5 discloses "a denture base resin composition comprising: (a) a polymerizable monomer and/or oligomer having a modulus of elasticity when polymerized of 0.25 to 3.00 GPa; (b) an organic filler and/or organic-inorganic composite filler having a modulus of elasticity of 0.25 to 3.00 GPa; and (c) a polymerization initiator including a heating polymerizable polymerization initiator and/or a photo-polymerizable polymerization initiator, characterized in that the denture base resin composition is in a one-paste state". According to Patent Document 5, the above-mentioned denture base resin composition is considered to have, in addition to the characteristics of the one-paste type as disclosed in Patent Document 4, a feature that a cured body having excellent flexural strength and elastic energy characteristics as well as excellent impact resistance can be obtained due to use of a filler having a moderately low modulus of elasticity as a filler.

Patent Document 1: Japanese Unexamined Patent Application, Publication No. H11-335222
Patent Document 2: Japanese Examined Patent Application Publication No. H04-042364
Patent Document 3: Japanese Unexamined Patent Application, Publication No. 2000-175941
Patent Document 4: Japanese Unexamined Patent Application, Publication No. 2000-254152
Patent Document 5: Japanese Unexamined Patent Application, Publication No. 2002-104912
Patent Document 6: Japanese Unexamined Patent Application, Publication No. 2013-87076
Patent Document 7: Japanese Unexamined Patent Application, Publication No. 2004-203773
Patent Document 8: Japanese Unexamined Patent Application, Publication No. 2009-179612

DISCLOSURE OF THE INVENTION

Problems to be Solved by the Invention

As described above, the one-paste type denture base curable composition overcomes the disadvantages possessed by the powder-liquid type or two-paste type denture base curable composition, and in particular, using the denture base resin composition disclosed in Patent Document 5, a cured body having excellent flexural strength as well as impact resistance can be obtained. However, conventional one-paste type denture base curable compositions were not always satisfactory in terms of toughness of the obtained cured bodies. In addition, depending on the filler used, it was difficult to control paste property and the strengths of the obtained cured bodies were low in some cases.

Supplementing with regard to the paste property, because a paste type denture base curable composition is often handled by hands with gloves on due to characteristics thereof, it is necessary to suppress stickiness so as not to adhere to the gloves. On the other hand, the paste-type denture base curable composition needs to be sticky enough to adhere to a gypsum model when used in the production of a new denture base and to a denture base when used in relining or repairing the denture base. In other words, the one-paste type denture base curable composition is required to have paste property having an appropriate viscosity such that it does not adhere to a glove but adheres to a gypsum model or a denture base.

In view of such circumstances, an object of the present invention is to provide a one-paste type denture base curable composition, which can provide a cured body having high strength and toughness and which has good paste operability.

Means for Solving the Problems

Since the cured body of a denture base curable composition is a composite material of a (meth)acrylic polymer used as a filler having a low modulus of elasticity and a cured body of a polymerizable monomer serving as a matrix, the interfacial state between these materials is considered to affect toughness. Therefore, the present inventors considered that using a porous organic crosslinked polymer as an organic filler would enable a higher strength due to cross-linking to be achieved, and have made intensive studies.

As a result, the following findings could be obtained: (1) by using a porous organic crosslinked polymer, the desired effects can be obtained in some cases; (2) the desired effects cannot be obtained in some cases depending on the type of the porous organic crosslinked polymer; and (3) when a large amount of a non-porous organic crosslinked polymer coexists, hardness of the paste easily changes during storage. As a result of further investigation based on these findings, the present inventors have found that, by using a monomer-absorbing porous organic crosslinked polymer having a specific monomer absorption amount with respect to a polymerizable monomer to be actually used, flexural strength (strength) and breaking energy (toughness) of the cured body can be improved and the paste property can be improved, and that the change in paste hardness during storage is reduced and storage stability is improved by limiting the content of the non-porous organic crosslinked polymer to no greater than a specific amount, thereby completing the present invention.

In other words, the present invention provides a denture base curable composition in a paste state, including (A) a (meth)acrylic monomer, (B) a monomer-absorbing porous organic crosslinked polymer capable of absorbing the (meth) acrylic monomer (A), and (C) a polymerization initiator selected from a photo-polymerization initiator and a thermal polymerization initiator. In the denture base curable composition, the content of the monomer-absorbing porous organic crosslinked polymer (B) is 20 to 80 parts by mass per 100 parts by mass of the (meth)acrylic monomer (A), and an absorption amount $R_{Ab}$, which represents an amount of the (meth)acrylic monomer (A) absorbed per unit amount of the monomer-absorbing porous organic crosslinked polymer (B), is 1.5 or more. $R_{Ab}$ is defined by the following equation:

$$R_{Ab}=\{(g-A)/(g-B)\}$$

in which g–A (unit: g) represents an amount of the (meth) acrylic monomer (A) absorbed by the monomer-absorbing porous organic crosslinked polymer (B) in an amount of g–B (unit: g), and is measured according to JIS K5101-13-1: 2004.

Note that, with regard to the porous organic polymer, an example (see, for example, Patent Document 6) in which a porous organic polymer is formulated as a filler in a dental mucosa adjusting material containing a plasticizer and a water-soluble organic solvent; an example (see, for example, Patent Document 7) in which an porous organic polymer is formulated in a dental adhesive as a catalyst carrier; and an example (see, for example, Patent Document 8) in which a porous organic polymer is formulated in a dental adhesive containing an acidic group-containing monomer, water, and a polymerization initiator are known. However, to the best of our knowledge, there is no example in which the porous organic polymer is formulated in a denture base curable composition consisting of a non-aqueous composition which is substantially free of water.

Effects of the Invention

According to the present invention, it is possible to provide a one-paste type denture base curable composition, in which a cured body obtained therefrom has high strength and toughness and which has good operability as a paste.

PREFERRED MODE FOR CARRYING OUT THE INVENTION

Below, embodiments of the present invention are described in detail. However, the present invention is not limited to the following embodiments.

In this specification, unless otherwise specified, the notation "x to y" using the numerical values x and y means "x or more and y or less". In such a notation, when only a numerical value y is given a unit, the unit shall be also applied to the numerical value x.

Additionally, in this specification, the term "(meth) acrylic" means both "acrylic" and "methacrylic". Similarly, the term "(meth) acrylate" means both "acrylate" and "methacrylate", and the term "(meth) acryloyl" means both "acryloyl" and "methacryloyl".

<Denture Base Curable Composition>

The denture base curable composition as described in the present embodiment is a paste state composition including (A) a (meth)acrylic monomer (hereinafter, also referred to as "component (A)" as appropriate), (B) a monomer-absorbing porous organic crosslinked polymer capable of absorbing the (meth)acrylic monomer (A) (hereinafter, also referred to as "component (B)" as appropriate), and (C) a polymerization initiator selected from a photo-polymerization initiator and a thermal polymerization initiator (hereinafter, also referred to as "component (C)" as appropriate). The content of the monomer-absorbing porous organic crosslinked polymer (B) is 20 to 80 parts by mass per 100 parts by mass of the (meth)acrylic monomer (A), and an absorption amount $R_{Ab}$ representing an amount of the (meth)acrylic monomer (A) absorbed per unit amount of the monomer-absorbing porous organic crosslinked polymer (B) is 1.5 or more. $R_{Ab}$ is defined by the following equation:

$$R_{Ab}=\{(g-A)/(g-B)\}$$

in which g–A (unit: g) represents an amount of the (meth) acrylic monomer (A) absorbed by the monomer-absorbing porous organic crosslinked polymer (B) in an amount of g–B (unit: g), and is measured according to JIS K5101-13-1: 2004. The denture base curable composition as described in the present embodiment preferably further includes (D) a (meth)acrylic non-crosslinked polymer (hereinafter, also referred to as "component (D)" as appropriate) to be described later. In addition, the denture base curable composition as described in the present embodiment may further include (B') a non-porous organic crosslinked polymer (hereinafter, also referred to as "component (B')" as appropriate) to be described later.

Herein, the term "paste" refers to a non-settling non-Newtonian fluid, and the term "paste state" in this specification refers to a highly viscous paste having plastic deformability, particularly a highly viscous paste of a non-aqueous type. The denture base curable composition (paste state composition) as described in the present embodiment includes, as main components, a mixture of the component (A), the component (B), and the component (D), when the component (D) is included as an optional component, and preferably includes, as main components, a mixture of the component (A) and the component (B) when the component (D) is not included. Note that the recitation "as main components" means that when a total mass of a composition is set to 100 parts by mass, a total mass of the main components is 80 parts by mass or more, and preferably 90 parts by mass or more.

The denture base curable composition as described in the present embodiment has an advantage of the curable composition for a one-paste type denture base curable composition that does not require bothersome operations of metering and kneading, and also, it is possible to provide a cured body having both high flexural strength (strength) and high breaking energy (toughness).

Further, a denture base curable composition including a predetermined amount of the component (D) (5 to 40 parts by mass per 100 parts by mass of the component (A)) has paste property such that it does not adhere to a glove but adheres to a gypsum model or a denture base, and also has excellent operability. Generally, paste viscosity is adjusted by the amount of filler (an organic filler, an inorganic filler, an organic-inorganic composite filler, or the like) included. In order to have the paste characteristics as described above, it is necessary to increase a formulated amount of the filler, but the toughness of the cured body tends to decrease with an increase in the amount of the filler. Contrary to this, by the denture base curable composition as described in the present embodiment, a preferable paste state as described above can be obtained, while contrarily increasing the toughness of the cured body.

Further, a denture base curable composition including no component (B') or only 10 parts by mass or less, if any, per 100 parts by mass of the component (A) has an effect that paste hardness thereof does not change with time and can be stably stored for a long period of time.

Without being bound by any particular theory, the present inventors presume that the mechanism by which the denture base curable composition as described in the present embodiment exhibits the above-described excellent effects is as follows.

That is, the reason why flexural strength (strength) of a cured body is high is that a crosslinked polymer having a high modulus of elasticity is used as an organic filler. Further, the reason why the toughness of the cured body increases despite the use of the crosslinked polymer is that the (meth)acrylic monomer (A) penetrates into the inside of the pores of the monomer-absorbing porous organic crosslinked polymer (B) and cures, which generates an anchor effect, thereby increasing an interfacial bonding strength between the matrix and the organic filler in the cured body.

Further, as the reason why a good paste state could be achieved, the following reason can be considered. In a system including a (meth)acrylic non-crosslinked polymer (D), due to an interaction with the (meth)acrylic monomer (A), specifically, due to a part of the component (D) being dissolved in the component (A), or the component (D) being swollen with the component (A) and softened, the system becomes adjustable to a good state, whereas since the crosslinked polymer is poor in such an interaction, formulating a large amount of the crosslinked polymer is usually considered to narrow such an adjustable range of the paste state. However, when the monomer-absorbing porous organic crosslinked polymer (B) is used, the component (A) penetrates into the pores and interaction similar to the above-mentioned interaction occurs, which is considered to make it possible to keep the above-mentioned adjustable range wide, and thereby a good paste state can be achieved.

Further, the reason why the storage stability of the paste (the property that the paste does not become hard even if stored for a long period of time) is enhanced is considered to be due to the matrix penetrating into the pores of the monomer-absorbing porous organic crosslinked polymer (B) and not aggregating within the paste, thereby the state immediately after the preparation can be maintained, whereas in the case of a paste with poor storage stability, the matrix generally has poor interaction with the crosslinked polymer, and therefore aggregates and settles in the paste, and thereby the paste may become hard in some cases.

Hereinafter, the respective components included in the denture base curable composition as described in the present embodiment are described in detail.

[(Meth)Acrylic Monomer (A)]

As the (meth)acrylic monomer, (meth)acrylic monomers commonly used for dental use can be used without any particular limitation. Specific examples of the (meth)acrylic monomers include: monofunctional (meth)acrylic monomers, such as methyl (meth)acrylate, ethyl (meth)acrylate, hydroxyethyl (meth)acrylate, tetrahydrofurfuryl (meth)acrylate, 2-(meth)acryloyloxyethyl propionate, acetoacetoxyethyl (meth)acrylate, etc.; bifunctional (meth)acrylic monomers, such as 1,6-bis((meth)acryloylethyloxycarbonylamino)trimethylhexane, 2,2-bis((meth)acryloyloxy(phenyl)propane, ethyleneglycol di(meth)acrylate, 1,6-hexanediol di(meth)acrylate, 1,9-nonanediol di(meth)acrylate, etc.; trifunctional (meth)acrylic monomers, such as trimethylolmethane tri(meth)acrylate, trimethylolethane tri(meth)acrylate, trimethylolpropane tri(meth)acrylate, pentaerythritol tri(meth)acrylate, etc.; and the like. One type of these (meth)acrylic monomers may be used alone, and two or more types thereof may be used in combination. In particular, when a monofunctional (meth)acrylic monomer and a (meth)acrylic monomer having two or more functionalities are used in combination, it is preferable to formulate a larger amount of a (meth)acrylic monomer having two or more functionalities than a monofunctional (meth)acrylic monomer, because mechanical properties such as strength and durability of the obtained cured body can be improved.

The content of the component (A) is preferably 40 to 80 parts by mass, and more preferably 50 to 70 parts by mass, when the total mass of the curable composition for the denture base curable composition as described in the present embodiment is set to 100 parts by mass.

[Monomer-Absorbing Porous Organic Crosslinked Polymer (B)]

As the monomer-absorbing porous organic crosslinked polymer, a monomer-absorbing porous organic crosslinked polymer including a polymer that has a crosslink, that is composed of a particulate or powdery (aggregate of fine particles) organic material at an atmospheric ambient temperature, that has pores within the particles communicating with the outside, and that has, on the surface of the particles, a large number of pores through which the (meth)acrylic monomer (A) can penetrate is used. Particularly in the present embodiment, from the viewpoint of improving strength, the monomer-absorbing porous organic crosslinked polymer (B) that has an absorption amount $R_{Ab}$ of 1.5 or more, preferably 2.0 to 5.0 is used. Herein, $R_{Ab}$ represents an amount of the (meth)acrylic monomer (A) absorbed per unit amount of the monomer-absorbing porous organic crosslinked polymer (B) and is defined by the following equation:

$$R_{Ab} = \{(g-A)/(g-B)\}$$

in which g-A (unit: g) represents an amount of the (meth)acrylic monomer (A) absorbed by the monomer-absorbing porous organic crosslinked polymer (B) in an amount of g-B (unit: g). $R_{Ab}$ is measured according to JIS K5101-13-1: 2004 (ISO), except that refined linseed oil is changed to the (meth)acrylic monomer (A).

Note that the absorption amount $R_{Ab}$ is determined according to "Refined Linseed Oil Method" described in JIS K5101-13-1: 2004, except that the (meth)acrylic monomer (A) (when a mixture of two or more types of monomers is used, the mixture having the same composition) used in the denture base curable composition as described in the present embodiment is used instead of refined linseed oil. Specifically, a predetermined amount [$M_B$ (g)] of the monomer-absorbing porous organic crosslinked polymer (B) is placed on a glass plate, and the monomer of the component (A) is gradually added from the burette in an amount of four or five drops at a time. Each time the monomer is added, the monomer is kneaded into the polymer with a palette knife. These are repeated and the addition of drops is continued until a mass of monomer and polymer is formed. Thereafter, the monomer is added drop by drop, and the operation is repeated so that the monomer and the polymer are thoroughly kneaded. Then, the point at which the paste has reached a smooth hardness is defined as an end point, and the amount [$M_A$ (g)] of the monomer of the component (A) used up to the end point is measured. When doing so, time required for the operation to the end point shall be within 25 minutes. Then, the absorption amount $R_{Ab}$ is determined according to the following equation:

$$R_{Ab}(g/g) = M_A(g)/M_B(g).$$

The absorption amount $R_{Ab}$ determined as described above is a parameter representing a critical ratio of the component (A) and the monomer-absorbing porous organic crosslinked polymer (B) at which the monomer-absorbing porous organic crosslinked polymer (B) and the monomer of the component (A) that has penetrated into the inside of the monomer-absorbing porous organic crosslinked polymer (B) begin to turn into a smooth paste state. As can be understood from the simplicity of the operation, $R_{Ab}$ does not mean a strictly defined critical point, but is a measure relating to the ability of the monomer-absorbing porous organic crosslinked polymer (B) to absorb the component (A). Actually, the denture base curable composition as described in the present embodiment has been confirmed to be a paste state composition in some cases, even when the formulated amount of the (meth)acrylic monomer (A) is less than the amount obtained by calculating as the product of the formulated amount of the monomer-absorbing porous organic crosslinked polymer (B) multiplied by the absorption amount $R_{Ab}$ (hereinafter, also referred to as "calculated total absorption amount").

Although details of the reason for the denture base curable composition existing in a paste state even when an amount of the component (A) is less than the calculated total absorption amount are unclear, the reason is considered to be due to the difference in the kneading conditions or kneading time. In other words, at the time of measuring the absorption amount, kneading is performed with a pallet knife and measurement is performed in a short time (within 25 minutes), it is, therefore, considered that there is also a monomer held between polymer particles of the component (B) which remains in a partially aggregated state, and thus there is a possibility that the absorption amount is estimated to be higher than the actual absorption amount. On the other hand, when preparing the denture base curable composition as described in the present embodiment, kneading is often performed using a mortar or a mechanical kneading device such as a planetary mixer or a kneader. Therefore, as a strong shearing force is considered to be applied during kneading, a high degree of uniformity can be achieved. Further, a portion of the monomer once absorbed into the pores is released by an extrusion effect due to the shearing force or an enlargement of a pore diameter due to heat generation or swelling, or the like, and thereby paste formation occurs.

Although there is no particular limitation on the material of the monomer-absorbing porous organic crosslinked polymer, crosslinked polyalkyl (meth)acrylates, such as crosslinked polymethyl methacrylate, crosslinked polyethyl methacrylate, crosslinked polymethyl acrylate, etc.; polystyrene, polyvinyl chloride; and the like are preferable from the viewpoint of affinity with the (meth)acrylic monomer (A). Further, it is also possible to use a porous crosslinked polymer described in Japanese Examined Patent Application, Publication No. H4-51522, Japanese Unexamined Patent Application, Publication No. 2002-265529, and the like. In addition, commercially available products such as "Technopolymer MBP-8" (Sekisui Kasei Co., Ltd.) can also be used.

The average pore diameter of the monomer-absorbing porous organic crosslinked polymer is preferably 1 to 100 nm, and more preferably 5 to 50 nm. The average pore diameter means an average diameter of pores formed on the surface of the primary particles, rather than aggregated pores of the secondary particles formed by aggregation of the particles. The average pore size can be calculated from the pore distribution of particles measured using a pore distribution measuring apparatus by a mercury pressure intrusion method. When the average pore diameter of the monomer-absorbing porous organic crosslinked polymer is 1 nm or more, the anchor effect in the cured body increases with an increase in the amount of penetration of the (meth)acrylic monomer (A) into the pores, and sufficient strength tends to be easily obtained. Further, when the average pore diameter of the monomer-absorbing porous organic crosslinked polymer is 100 nm or less, the anchor effect increases, and sufficient strength tends to be easily obtained.

The average particle diameter of the monomer-absorbing porous organic crosslinked polymer is preferably 1 to 50 μm, and more preferably 3 to 30 μm. The average particle size means an average particle size of primary particles and is measured using a particle size distribution measuring apparatus by a laser diffraction and scattering method. When the average particle diameter of the monomer-absorbing porous organic crosslinked polymer is 1 μm or more, stickiness of the paste before curing is suppressed, and operability tends to be improved. Further, when the average particle diameter of the monomer-absorbing porous organic crosslinked polymer is 50 μm or less, the specific surface area increases, and sufficient strength and toughness tend to be easily obtained in the cured body. Note that the particle shape is not particularly limited and may be a pulverized particle or a spherical particle.

The content of the component (B) is 20 to 80 parts by mass per 100 parts by mass of the component (A). When the content of the component (B) is less than 20 parts by mass, sufficient strength tends to be difficult to be obtained due to the anchor effect being lowered. On the other hand, when the content of the component (B) is more than 80 parts by mass, not only does the cured body become hard and brittle, but also the paste becomes hard and shaping tends to be difficult.

Note that, in addition to the above-mentioned formulation composition, it is preferable that the denture base curable composition as described in the present embodiment further satisfies the condition that the product obtained by multiplying the content (unit: g) of the monomer-absorbing porous organic crosslinked polymer (B) per unit amount (unit: g) of the (meth)acrylic monomer (A) by the absorption amount $R_{Ab}$ is 0.65 to 1.65.

[Non-Porous Organic Crosslinked Polymer (B')]

The denture base curable composition as described in the present embodiment may further contain a non-porous organic crosslinked polymer within a range that does not inhibit the effect of the present invention. The non-porous organic crosslinked polymer is in a form of particles each having no pores or a small number of pores on its surface and has an absorption amount $R_{Ab}$ determined as described above of less than 1.5.

The non-porous organic crosslinked polymer does not easily dissolve in or swell with the (meth)acrylic monomer (A) and has poor interaction with the matrix, so that the non-porous organic crosslinked polymer may aggregate and settle in the paste and the paste becomes hard in some cases. Therefore, when a large amount of the non-porous organic crosslinked polymer is formulated, properties and state of the paste may change during storage (specifically, it becomes hard), and the operability of the paste decreases in some cases. Therefore, the content of the component (B') is preferably 10 parts by mass or less per 100 parts by mass of the component (A), and more preferably not included.

[Polymerization Initiator (C)]

The denture base curable composition as described in the present embodiment contains a photo-polymerization initiator and/or a thermal polymerization initiator as a polymerization initiator to make it a one-paste type and does not include any or substantially any chemical polymerization initiator. Note that 'not include substantially any' means that it is acceptable to include an extremely small amount within a range that does not adversely affect storage stability and does not affect the effects of the present invention.

As the photo-polymerization initiator and the thermal polymerization initiator, those used in the dental field can be used without any particular limitation.

Specific examples of the photo-polymerization initiator include: benzoin alkyl ethers, such as benzoin methyl ether, benzoin ethyl ether, benzoin isopropyl ether, etc.; benzyl ketals, such as benzyl dimethyl ketal, benzyl diethyl ketal, etc.; diaryl ketones such as benzophenone, anthraquinone, thioxanthone, etc.; α-diketones such as diacetyl, benzyl, camphorquinone, 9,10-phenanthraquinone, etc.; bisacylphosphine oxides, such as bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis(2,4,6-trimethylbenzoyl)-phenylphosphine oxide, etc.; and the like. One type of these photo-polymerization initiators may be used alone, or two or more types thereof may be used in combination.

When a photo-polymerization initiator is used as a polymerization initiator, it is preferable to use the photo-polymerization initiator in combination with a reducing compound. Suitably usable reducing compounds include: tertiary amines such as 2-(dimethylamino)ethyl methacrylate, ethyl p-N,N-dimethylaminobenzoate, N-methyldiethanolamine, dimethylaminobenzaldehyde, terephthalaldehyde, etc.; sulfur-containing compounds such as 2-mercaptobenzoxazole, 1-decanethiol, thiosalicylic acid, thiobenzoic acid, etc.; N-phenylalanine; and the like.

In addition, in order to further enhance the activity of the photo-polymerization initiator, adding a photoacid generator is also a preferred embodiment. Examples of the photoacid generator include diaryliodonium salt-based compounds, sulfonium salt-based compounds, sulfonate ester compounds, halomethyl-substituted-S-triazine-derivatives, and pyridinium salt-based compounds, etc. When a photoacid generator is used, α-diketones such as camphorquinone, etc. are preferred as the photo-polymerization initiator, and reducing compounds such as ethyl p-N,N-dimethylaminobenzoate are more preferably used in combination.

Specific examples of the thermal polymerization initiator include peroxides such as benzoyl peroxide, p-chlorobenzoyl peroxide, tert-butyl peroxy-2-ethylhexanoate, tert-butyl peroxydicarbonate, and diisopropyl peroxydicarbonate, etc.; azo compounds such as azobisisobutyronitrile, etc.; and the like. One type of these thermal polymerization initiators may be used alone, or two or more types thereof may be used in combination.

The content of the component (C) may be any catalyst amount (that is, an amount which exhibits a function as a polymerization initiator and allows sufficient polymerization to occur). The specific amount thereof varies depending on the type of the polymerization initiator, and therefore cannot be generally defined, and is usually 0.05 to 5 parts by mass, and preferably 0.1 to 3 parts by mass, per 100 parts by mass of the (meth)acrylic monomer (A).

[(Meth)acrylic Non-Crosslinked Polymer (D)]

It is preferred that the denture base curable composition as described in the present embodiment further includes (meth)acrylic non-crosslinked polymer (D) so that the denture base curable composition easily achieves good paste property.

As the (meth)acrylic non-crosslinked polymer (D), a non-crosslinked (having no crosslinking) (meth)acrylic polymer that is generally used for dental use and that is granular or powdery at atmospheric ambient temperature can be used without any particular limitation. Examples of the (meth)acrylic non-crosslinked polymer (D) include homopolymers or copolymers of methyl (meth)acrylate, ethyl (meth)acrylate, tert-butyl (meth)acrylate, n-butyl (meth)acrylate, lauryl (meth)acrylate, dodecyl (meth)acrylate, stearyl (meth)acrylate, cyclohexyl (meth)acrylate, benzyl (meth)acrylate, isobornyl (meth)acrylate, isopropyl (meth)acrylate, 2-hydroxyethyl (meth)acrylate, 3-hydroxypropyl (meth)acrylate, 2-hydroxy-1,3-di(meth)acryloyl oxypropane, isobutyl (meth)acrylate, butoxyethyl (meth)acrylate, tetrahydrofurfuryl (meth)acrylate, glycidyl (meth) acrylate, 2-methoxyethyl (meth)acrylate, 2-ethylhexyl (meth)acrylate, etc.; copolymers of the (meth)acrylic monomer and other polymerizable monomers, such as poly(styrene-ethyl methacrylate), etc.; and the like. One type of these (meth)acrylic non-crosslinked polymers may be used alone, or two or more types thereof may be used in combination.

As the (meth)acrylic non-crosslinked polymer (D), those having solubility in the (meth)acrylic monomer (A) are preferred because adjustment of the paste property is easy, the paste property does not easily change during storage, and a decrease in strength of the cured body does not easily occur. Specifically, it is preferable to use such a component (D) which when formulated with 100 parts by mass of the component (A) completely dissolves at 45° C., when visually judged.

The average molecular weight of the (meth)acrylic non-crosslinked polymer (D) is not particularly limited. From the viewpoint of solubility and ease of adjustment of the paste property, the mass average molecular weight is preferably 50,000 to 1,000,000, and more preferably 100,000 to 700,000. Note that the mass average molecular weight in this specification means a standard polystyrene-converted molecular weight measured by gel permeation chromatography (GPC).

The average particle diameter of the (meth)acrylic non-crosslinked polymer (D) is not particularly limited. However, when the average particle diameter of the (meth)acrylic non-crosslinked polymer (D) is too large, it is slow to dissolve in the (meth)acrylic monomer (A). Then, it takes a long time to manufacture and this lowers the working efficiency. Therefore, the average particle diameter of the (meth)acrylic non-crosslinked polymer (D) is preferably 100 μm or less.

The content of the (meth)acrylic non-crosslinked polymer (D) is preferably from 5 to 40 parts by mass, and more preferably from 15 to 30 parts by mass, per 100 parts by mass of the (meth)acrylic monomer (A).

[Other Components]

The denture base curable composition as described in the present embodiment may further contain other components within a range that does not inhibit the effects of the present invention. Other components include inorganic fillers such as calcium carbonate, magnesium oxide, barium sulfate, titanium oxide, potassium titanate, aluminum hydroxide, silica powder, glass powder, diatomaceous earth, silica, calcium silicate, talc, alumina, mica, and quartz glass, etc.; particulate organic-inorganic composite fillers obtained by adding a polymerizable monomer to inorganic particles to change the obtained mixture to a paste state, followed by polymerization and pulverization; polymerization inhibitors such as butylhydroxytoluene and methoxyhydroquinone, etc.; ultraviolet absorbers such as 4-methoxy-2-hydroxybenzophenone, 2-(2-benzotriazole)-p-cresol, etc.; polymerization modifiers such as α-methyl styrene dimer, etc.; dyes, pigments, fragrances; and the like.

[Preparation Method]

The method for preparing the denture base curable composition as described in the present embodiment is not particularly limited, and each component may be weighed in a predetermined amount and mixed as appropriate. However, in a case in which the denture base curable composition as described in the present embodiment contains the component (D), it is preferable that the polymer particles serving as the component (D) be dissolved in the component (A) in advance. Specifically, a method is preferred in which the component (C), the component (D), and other additives are dissolved in the component (A), and then the obtained mixture is mixed with the component (B) and other fillers to be formulated, if necessary, to obtain a denture base curable composition in a paste state.

The obtained denture base curable composition is preferably stored in a light shielding container in order to prevent deterioration during storage, particularly when a photopolymerization initiator is used. There is no particular limitation on the paste form, and the denture base curable composition molded into a bar, a horseshoe shape, a sheet, a sphere, a prism, or the like may be stored in a container, or the denture base curable composition may be stored in a tube, a bottle, or the like as it is without molding.

[Use Method]

The denture base curable composition as described in the present embodiment can be used as a denture base resin, a denture base hard relining material, a denture base repairing resin, or the like according to known methods. For example, when a denture base is newly created, an impression in an oral cavity of a patient is obtained to prepare a gypsum model, and a denture base portion is formed using the denture base curable composition as described in the present embodiment on the gypsum model and is set in an articulator to arrange artificial teeth, followed by polymerization-curing by light irradiation or heating, further followed by shape correction and polishing. When repairing a plate denture that does not fit correctly, an adhesive and a separating agent are applied as required to the denture base which has become poorly-fitting with the oral cavity of the patient, and the denture base curable composition as described in the present embodiment is applied, adjusted into the oral cavity of the patient, and then polymerized and cured by light irradiation or heating, followed by shape correction and polishing. When relining a mucosa face, the denture base curable composition as described in the present embodiment may be applied thinly. When extending the denture base curable composition on the denture base, the denture base curable composition may be applied, in a manner that the paste in a rod shape is wound around.

<Kit>

A kit as described in the present embodiment includes the denture base curable composition as described in the present embodiment as a denture base hard relining material or denture base repairing resin; and a liquid adhesive that is used for adhesion with the denture base and that includes (a) a (meth)acrylic non-crosslinked polymer (hereinafter, also referred to as "component (a)" as appropriate), (b) a (meth) acrylic monomer (hereinafter, also referred to as "component (b)" as appropriate), and (c) an organic solvent (hereinafter, also referred to as "component (c)" as appropriate). The liquid adhesive may further contain (d) a polymerization initiator (hereinafter, also referred to as "component (d)" as appropriate) to be described later.

When using the denture base curable composition as described in the present embodiment as a denture base hard relining material or denture base repairing resin, an adhesive is commonly applied to a denture base, and then the denture base curable composition as described in the present embodiment is applied and polymerized and cured by photoirradiation or heating. The denture base curable composition as described in the present embodiment can be firmly adhered to the denture base using a liquid adhesive commonly used in the dental field.

The liquid adhesive provided in the kit according to the present embodiment is not particularly limited as long as it contains the component (a) to the component (c) and contains the component (d) if necessary. As the component (a), the component (b), and the component (d), the components described above as the component (D), the component (A), and the component (C), respectively, can be used without any particular limitation.

Examples of the organic solvent (c) include non-halogen organic solvents such as hydrocarbon compounds such as hexane, heptane, pentane, etc.; aromatic hydrocarbon compounds such as toluene, xylene, etc.; alcohol compounds such as ethanol, 1-propanol, 2-propanol, 1-butanol, 2-butanol, etc.; ether compounds such as diethyl ether, tetrahydrofuran, tert-butyl methyl ether, etc.; ketone compounds such as acetone, methyl ethyl ketone, methyl isobutyl ketone, etc.; ester compounds such as ethyl formate, methyl acetate, ethyl acetate, propyl acetate, isopropyl acetate, etc.; and the like. One type of these organic solvents may be used alone, or two or more types thereof may be used in combination.

Examples of denture bases to be bonded include a (meth) acrylic denture base. The (meth)acrylic denture base is generally composed mainly of polymethyl methacrylate, and a part thereof may be copolymerized with ethyl methacrylate, styrene, or the like, or may be crosslinked by a crosslinking agent such as ethylene glycol dimethacrylate.

<Denture Base and Plate Denture>

The denture base as described in the present embodiment includes the cured body of the denture base curable composition as described in the present embodiment. Since the cured body of the denture base curable composition as described in the present embodiment has excellent strength and toughness, the denture base containing this cured body has also excellent strength and toughness.

The denture base as described in the present embodiment may be made of the cured body of the denture base curable composition as described in the present embodiment in its entirety or may be partially made of the cured body of the denture base curable composition as described in the present embodiment. Examples of the former include a denture base newly created using the denture base curable composition as described in the present embodiment. Examples of the latter include a denture base reformed or repaired using the denture base curable composition as described in the present embodiment.

In addition, the denture base as described in the present embodiment may be a denture base for a complete denture (full denture), or may be a denture base for a removable partial denture (partial denture). In addition, the denture base as described in the present embodiment may be a denture base for an upper jaw, may be a denture base for a lower jaw, or may be a denture base for both of them.

Plate denture as described in the present embodiment is provided with the denture base as described in the present embodiment, and an artificial tooth fixed to this denture base. The plate denture as described in the present embodiment may be a completely denture or removable partial denture. In other words, the plate denture according to the present embodiment may be provided with at least one artificial tooth. In addition, the plate denture as described in the present embodiment may be a denture for an upper jaw, may be a denture for a lower jaw, or may be a denture for both of them.

EXAMPLES

Below, the Examples of the present invention are described, but the present invention is not limited to these Examples.

Firstly, names, characteristics, abbreviations (when abbreviations are used) and the like of the respective components used in the Examples and the Comparative Examples are indicated.

[(Meth)acrylic Monomer (A), (b)]
    HPr: 2-methacryloyloxyethyl propionate (monofunctional polymerizable monomer)
    ND: Nonamethylene diol dimethacrylate (bifunctional polymerizable monomer)
    UDMA: 1,6-bis(methacryloylethyloxycarbonylamino) trimethylhexane (bifunctional polymerizable monomer
    TT: Trimethylolpropane trimethacrylate (trifunctional polymerizable monomer)
    TMMT: Tetramethylolmethane tetramethacrylate (tetrafunctional polymerizable monomer)

[Monomer-Absorbing Porous Organic Crosslinked Polymer (B)]

Abbreviations, components, average particle diameters, and average pore diameters of the polymers used are indicated in Table 1

TABLE 1

| Abbreviation | Component | Average particle diameter [μm] | Average pore diameter [nm] | Manufacturer |
|---|---|---|---|---|
| PMMA-P8 | Polymethyl methacrylate | 8 | 20 | Sekisui Kasei Co., Ltd. |
| PMMA-PH | Polymethyl methacrylate | 8 | 20 | Sekisui Kasei Co., Ltd. |
| PMMA-P20 | Polymethyl methacrylate | 20 | 20 | Sekisui Kasei Co., Ltd. |
| AC-P | Polyacrylate ester | 8 | 27 | Sekisui Kasei Co., Ltd. |

[(B') Non-Porous Organic Crosslinked Polymer (B')]
    PMMA-X: Polymethylmethacrylate (average particle diameter: 8 μm, manufactured by Sekisui Kasei Co., Ltd.)
    AC-X: Polyacrylate ester (average particle diameter: 8 μm, manufactured by Sekisui Kasei Co., Ltd.)

[Polymerization Initiator (C), (d)]
    CQ: Camphorquinone
    BPO: Benzoyl peroxide
    DMBE: Ethyl 4-(N,N-dimethylamino)benzoate

[(Meth)Acrylic Non-Crosslinked Polymer (D), (a)]
    PEMA: Polyethylmethacrylate (average particle diameter: 35 μm, mass-average molecular weight: 500,000)
    P(EMA-MMA): Polyethylmethacrylate-methyl methacrylate copolymer (ethyl methacrylate/methyl methacrylate=50/50, average particle diameter: 40 μm, mass average molecular weight: 1,000,000)
    PBMA: Polybutylmethacrylate (average particle diameter: 60 μm, mass average molecular weight: 150,000)

[Organic Solvent (c)]
    Acetone
    Ethyl Acetate

[Other Components]
    Silica: Spherical silica (treated with 3-methacryloyloxypropyl trimethoxysilane, average particle diameter: 1 μm)

Next, measurement methods of evaluation items in the Examples and the Comparative Examples are indicated below.

(1) Monomer Absorption Amount

The monomer absorption amount $R_{Ab}$ was determined using, in the "Refined Linseed Oil Method" described in JIS K5101-13-1: 2004, the (meth)acrylic monomer (A) (when two or more types of (meth)acrylic monomers were used, a monomer mixture of the same composition) used in the respective Examples or Comparative Examples, instead of using refined linseed oil. Specifically, a predetermined amount [$M_B$ (g)] of a monomer-absorbing porous organic crosslinked polymer (B) was placed on a glass plate, and the monomer of the component (A) was gradually added from the burette in an amount of four or five drops at a time. Each time the monomer was added, the monomer was kneaded into the polymer with a palette knife. These were repeated and the dropping was continued until a mass of monomer and polymer was formed. Thereafter, the monomer was added drop by drop, and the operation was repeated so that the monomer and the polymer were thoroughly kneaded. Then, the point at which the paste reached a smooth hardness is defined as an end point, and the amount [$M_A$ (g)] of the monomer of the component (A) used up to the end point was measured. Note that the operation was performed so that the time required for the operation to the end point was within 25 minutes. Then, the monomer absorption amount $R_{Ab}$ was determined according to the following equation:

$$R_{Ab}(g/g)=M_A(g)/M_B(g)$$

(2) Flexural Strength, Modulus of Elasticity, and Breaking Energy

A polytetrafluoroethylene mold of 30 mm×30 mm×2 mm was filled with paste. When a photo-polymerization initiator was used, a cured body was prepared by photo-irradiation for 5 minutes using a photo-polymerization device α light V (manufactured by Morita Co., Ltd.) for dental engineering in a state in which both surfaces were pressure-contacted with polyethylene film. When a heat-polymerization catalyst was used, the paste was immersed in water, in a state in which both surfaces were pressure-contacted with polyethylene film and heated for one hour after boiling to prepare a cured body. Then, after polishing the cured body with water-resistant abrasive paper of #800 and #1500, the cured body was cut into a 4 mm×30 mm×2 mm prismatic shape. The obtained cured body was immersed in water and left at 37° C. for 24 hours. This test piece was mounted on a test machine (Autograph AG-1, manufactured by Shimadzu Corporation), subjected to three-point bending test with a distance between the fulcrums of 20 mm, at a cross head speed of 1 ram/min, and flexural strength, modulus of elasticity, and breaking energy were measured.

(3) Paste Hardness

Paste was charged into a nut-like mold made of SUS, the surface was smoothed and the paste was left under shielding from light for 2 minutes to keep the temperature constant at 23° C. A φ5 mm bar made of SUS was mounted as a pressure-sensitive shaft on a Sun rheometer (manufactured by Sun Scientific Co., Ltd.), and was compressed to enter at a rate of 240 mm/minute to a depth of 2 mm. The maximum load [g] at this time was defined as the hardness of the paste. Measurements were performed on the following day on which the paste was prepared (initial), and after the paste was stored at 23° C. for one month (one month later).

(4) Paste Adhesiveness

The adhesiveness of paste was evaluated with gloves on, based on the following criteria:

A: Paste does not adhere to the gloves, but adheres to the denture base and gypsum.

B: Paste adheres to the gloves, but can be detached from the gloves once adhered to the denture base and gypsum.

C: Paste adheres to the gloves and does not adhere to the denture base and gypsum.

(5) Paste Property after One Month

Paste was stored at 23° C. for one month, and the paste property was evaluated based on the following evaluation criteria.

A: No change is observed compared to the state immediately after paste preparation.

B: Minor change is observed in viscosity compared to the state immediately after paste preparation.

C: Significant change in viscosity is observed compared to the state immediately after paste preparation.

(6) Bond Strength

A plate (15 mm×15 mm×2 mm) of the denture base resin (Acron, manufactured by GC Co., Ltd.) was prepared, and the plate was polished with water-resistant abrasive paper #800 to obtain an adherend. Adhesive was applied to the adherend using a brush, and was left to stand until the solvent component in the adhesive volatilized and dried. Then, a double-sided tape having a hole with a diameter of 3 mm was bonded on the adherend, and then, a paraffin wax having a hole with a diameter of 8 mm was bonded on the double-sided tape so as to have the same center. The holes were filled with the paste and photo-irradiated for 5 minutes using a photo-polymerization device α light V (manufactured by Morita Co., Ltd.) for dental engineering in a state of being pressure-contacted with polyethylene film, to prepare an adhesive test piece. After immersing the above adhesive test piece in water at 37° C. for 24 hours, the metal attachment was attached to the cured body, bond strength was measured using a tensile tester (Autograph, manufactured by Shimadzu Corporation) by pulling at a cross head speed of 2 mm/min. The average value of five test pieces was adopted as the bond strength (initial). In addition, the test piece prepared in the same manner as described above was subjected to a thermal shock test using a thermal shock tester (manufactured by Tokyo Giken Inc.), in which a cycle including immersing the test piece in water at 5° C. for 30 seconds and then in water at 55° C. for 30 seconds is repeated 10,000 times. With respect to the test piece after the thermal shock test, the bond strength was measured in the same manner as described above, and the average value of five test pieces was adopted as the bond strength (after durability test).

Example 1

Pastes were prepared according to the compositions indicated in Table 2, and adhesives were prepared according to the compositions indicated in Table 3, and evaluation of each of the physical properties was performed. The amount of each component in Table 2 and Table 3 is in parts by mass. Results are shown in Table 4.

TABLE 2

| Example No. | (A) (Meth)acrylic monomer | | (B) Monomer-absorbing porous organic crosslinked polymer | | (C) Polymerization initiator | | | | (D) (Meth)acrylic non-crosslinked polymer | | (B') Non-porous organic crosslinked polymer | |
|---|---|---|---|---|---|---|---|---|---|---|---|---|
| | Type | Amount | Type | Amount | Type | Amount | Type | Amount | Type | Amount | Type | Amount |
| Example 1 | HPr | 50 | ND | 50 | PMMA-P8 | 55 | CQ | 0.5 | DMBE | 0.5 | — | — |
| Example 2 | HPr | 50 | ND | 50 | PMMA-P20 | 80 | CQ | 0.5 | DMBE | 0.5 | — | — |
| Example 3 | HPr | 50 | ND | 50 | PMMA-P8 | 55 | CQ | 0.5 | DMBE | 0.5 | PEMA | 25 |
| Example 4 | HPr | 50 | ND | 50 | PMMA-PH | 45 | CQ | 0.5 | DMBE | 0.5 | PEMA | 25 |
| Example 5 | HPr | 50 | ND | 50 | PMMA-P20 | 70 | CQ | 0.5 | DMBE | 0.5 | PEMA | 25 |
| Example 6 | HPr | 50 | ND | 50 | AC-P | 55 | CQ | 0.5 | DMBE | 0.5 | PEMA | 25 |
| Example 7 | HPr | 50 | UDMA | 50 | PMMA-P8 | 55 | CQ | 0.5 | DMBE | 0.5 | PEMA | 25 |
| Example 8 | HPr | 80 | TT | 20 | PMMA-P8 | 55 | CQ | 0.5 | DMBE | 0.5 | PEMA | 25 |
| Example 9 | HPr | 50 | ND | 50 | PMMA-P8 | 55 | BPO | 1.0 | — | | PEMA | 25 |
| Example 10 | HPr | 50 | ND | 50 | PMMA-P8 | 55 | CQ | 0.5 | DMBE | 0.5 | P (EMA-MMA) | 25 |
| Example 11 | HPr | 50 | ND | 50 | PMMA-P8 | 55 | CQ | 0.5 | DMBE | 0.5 | PBMA | 25 |
| Example 12 | HPr | 50 | ND | 50 | PMMA-P8 | 55 | CQ | 0.5 | DMBE | 0.5 | PEMA | 5 |
| Example 13 | HPr | 50 | ND | 50 | PMMA-P8 | 55 | CQ | 0.5 | DMBE | 0.5 | PEMA | 15 |
| Example 14 | HPr | 50 | ND | 50 | PMMA-PH | 30 | CQ | 0.5 | DMBE | 0.5 | PEMA | 30 |
| Example 15 | HPr | 50 | ND | 50 | PMMA-PH | 20 | CQ | 0.5 | DMBE | 0.5 | PEMA | 40 |
| Example 16 | HPr | 50 | ND | 50 | PMMA-P8 | 55 | CQ | 0.5 | DMBE | 0.5 | PEMA | 25 | PMMA-X | 8 |
| Example 17 | HPr | 50 | ND | 50 | PMMA-P8 | 55 | CQ | 0.5 | DMBE | 0.5 | PEMA | 25 | | |
| Example 18 | HPr | 50 | ND | 50 | PMMA-P8 | 55 | CQ | 0.5 | DMBE | 0.5 | PEMA | 25 | | |
| Example 19 | HPr | 50 | ND | 50 | PMMA-P8 | 55 | CQ | 0.5 | DMBE | 0.5 | PEMA | 25 | | |
| Example 20 | HPr | 50 | ND | 50 | PMMA-P8 | 55 | CQ | 1.0 | DMBE | 1.0 | PEMA | 25 | | |
| Example 21 | HPr | 50 | ND | 50 | PMMA-P8 | 55 | CQ | 1.0 | DMBE | 1.0 | PEMA | 25 | | |
| Example 22 | HPr | 50 | ND | 50 | PMMA-P8 | 55 | CQ | 1.0 | DMBE | 1.0 | PEMA | 25 | | |
| Example 23 | HPr | 50 | ND | 50 | PMMA-P8 | 55 | CQ | 1.0 | DMBE | 1.0 | PEMA | 25 | | |

TABLE 3

| Example No. | (a) (Meth)acrylic non-crosslinked polymer | | (b) (Meth)acrylic monomer | | (c) Organic solvent | | | | (d) Polymerization initiator | |
|---|---|---|---|---|---|---|---|---|---|---|
| | Type | Amount | Type | Amount | Type | Amount | Type | Amount | Type | Amount |
| Example 1 | P (EMA-MMA) | 5.0 | TMMT | 5.0 | Ethyl acetate | 50.0 | Acetone | 50.0 | — | — |
| Example 2 | P (EMA-MMA) | 5.0 | TMMT | 5.0 | Ethyl acetate | 50.0 | Acetone | 50.0 | — | — |
| Example 3 | P (EMA-MMA) | 5.0 | TMMT | 5.0 | Ethyl acetate | 50.0 | Acetone | 50.0 | — | — |
| Example 4 | P (EMA-MMA) | 5.0 | TMMT | 5.0 | Ethyl acetate | 50.0 | Acetone | 50.0 | — | — |
| Example 5 | P (EMA-MMA) | 5.0 | TMMT | 5.0 | Ethyl acetate | 50.0 | Acetone | 50.0 | — | — |
| Example 6 | P (EMA-MMA) | 5.0 | TMMT | 5.0 | Ethyl acetate | 50.0 | Acetone | 50.0 | — | — |
| Example 7 | P (EMA-MMA) | 5.0 | TMMT | 5.0 | Ethyl acetate | 50.0 | Acetone | 50.0 | — | — |
| Example 8 | P (EMA-MMA) | 5.0 | TMMT | 5.0 | Ethyl acetate | 50.0 | Acetone | 50.0 | — | — |
| Example 9 | P (EMA-MMA) | 5.0 | TMMT | 5.0 | Ethyl acetate | 50.0 | Acetone | 50.0 | — | — |
| Example 10 | P (EMA-MMA) | 5.0 | TMMT | 5.0 | Ethyl acetate | 50.0 | Acetone | 50.0 | — | — |

TABLE 3-continued

| Example No. | (a) (Meth)acrylic non-crosslinked polymer Type | Amount | (b) (Meth)acrylic monomer Type | Amount | (c) Organic solvent Type | Amount | Type | Amount | (d) Polymerization initiator Type | Amount |
|---|---|---|---|---|---|---|---|---|---|---|
| Example 11 | P (EMA-MMA) | 5.0 | TMMT | 5.0 | Ethyl acetate | 50.0 | Acetone | 50.0 | — | — |
| Example 12 | P (EMA-MMA) | 5.0 | TMMT | 5.0 | Ethyl acetate | 50.0 | Acetone | 50.0 | — | — |
| Example 13 | P (EMA-MMA) | 5.0 | TMMT | 5.0 | Ethyl acetate | 50.0 | Acetone | 50.0 | — | — |
| Example 14 | P (EMA-MMA) | 5.0 | TMMT | 5.0 | Ethyl acetate | 50.0 | Acetone | 50.0 | — | — |
| Example 15 | P (EMA-MMA) | 5.0 | TMMT | 5.0 | Ethyl acetate | 50.0 | Acetone | 50.0 | — | — |
| Example 16 | P (EMA-MMA) | 5.0 | TMMT | 5.0 | Ethyl acetate | 50.0 | Acetone | 50.0 | — | — |
| Example 17 | P (EMA-MMA) | 2.5 | TMMT | 2.5 | Ethyl acetate | 50.0 | Acetone | 50.0 | CQ | 3.0 |
| Example 18 | P (EMA-MMA) | 2.5 | TMMT | 2.5 | Ethyl acetate | 50.0 | Acetone | 50.0 | CQ | 5.0 |
| Example 19 | P (EMA-MMA) | 2.5 | TT | 2.5 | Ethyl acetate | 50.0 | Acetone | 50.0 | — | — |
| Example 20 | P (EMA-MMA) | 2.5 | TT | 2.5 | Ethyl acetate | 35.0 | Acetone | 60.0 | — | — |
| Example 21 | P (EMA-MMA) | 2.5 | TT | 2.5 | Ethyl acetate | 95.0 | — | — | — | — |
| Example 22 | PEMA | 2.5 | TT | 2.5 | Ethyl acetate | 50.0 | Acetone | 50.0 | — | — |
| Example 23 | PMMA | 2.5 | TT | 2.5 | Ethyl acetate | 50.0 | Acetone | 50.0 | — | — |

TABLE 4

| Example No. | Monomer absorption amount [g/g] | Amount of (B) × absorption amount | Flexural strength [Mpa] | Modulus of elasticity [GPa] | Breaking energy [N·mm] | Paste hardness [g] Initial | One month later | Paste adhesiveness | Paste property one month later | Bond strength [MPa] Initial | After durability test |
|---|---|---|---|---|---|---|---|---|---|---|---|
| Example 1 | 2.4 | 132 | 80 | 1.5 | 95 | 620 | 650 | B | A | 9.3 | 9.4 |
| Example 2 | 1.7 | 136 | 60 | 1.5 | 68 | 1230 | 1235 | B | A | 8.2 | 7.3 |
| Example 3 | 2.4 | 132 | 78 | 1.7 | 90 | 3100 | 3150 | A | A | 9.5 | 9.2 |
| Example 4 | 3.3 | 149 | 82 | 1.6 | 124 | 1445 | 1440 | A | A | 8.9 | 8.5 |
| Example 5 | 2.3 | 161 | 61 | 1.5 | 71 | 3800 | 3810 | A | A | 7.9 | 7.8 |
| Example 6 | 1.7 | 94 | 62 | 1.2 | 120 | 1900 | 1930 | A | A | 8.1 | 7.9 |
| Example 7 | 2.1 | 116 | 80 | 1.7 | 126 | 4450 | 4430 | A | A | 8.4 | 8.4 |
| Example 8 | 2.5 | 138 | 83 | 1.8 | 75 | 2950 | 2980 | A | A | 8.2 | 8.0 |
| Example 9 | 2.4 | 132 | 75 | 1.7 | 92 | 3150 | 3110 | A | A | 9.4 | 9.3 |
| Example 10 | 2.4 | 132 | 75 | 1.7 | 82 | 3300 | 3350 | A | A | 8.9 | 8.5 |
| Example 11 | 2.4 | 132 | 70 | 1.5 | 104 | 2840 | 2850 | A | A | 7.9 | 7.3 |
| Example 12 | 2.4 | 132 | 79 | 1.5 | 93 | 1150 | 1210 | B | A | 8.5 | 8.4 |
| Example 13 | 2.4 | 132 | 80 | 1.6 | 92 | 2160 | 2250 | A | A | 8.8 | 8.6 |
| Example 14 | 3.3 | 99 | 68 | 1.4 | 75 | 3270 | 3260 | A | A | 8.0 | 8.2 |
| Example 15 | 3.3 | 66 | 60 | 1.5 | 95 | 3980 | 4000 | A | A | 7.6 | 7.7 |
| Example 16 | 2.4 | 132 | 73 | 1.7 | 84 | 3365 | 3750 | A | B | 8.6 | 8.4 |
| Example 17 | 2.4 | 132 | 78 | 1.7 | 90 | 3100 | 3150 | A | A | 11.0 | 10.3 |
| Example 18 | 2.4 | 132 | 78 | 1.7 | 90 | 3100 | 3150 | A | A | 12.3 | 11.9 |
| Example 19 | 2.4 | 132 | 78 | 1.7 | 90 | 3100 | 3150 | A | A | 10.2 | 11.0 |
| Example 20 | 2.4 | 132 | 81 | 1.8 | 78 | 3080 | 3100 | A | A | 12.6 | 13.1 |
| Example 21 | 2.4 | 132 | 81 | 1.8 | 78 | 3080 | 3100 | A | A | 10.7 | 10.1 |
| Example 22 | 2.4 | 132 | 81 | 1.8 | 78 | 3080 | 3100 | A | A | 11.2 | 10.3 |
| Example 23 | 2.4 | 132 | 81 | 1.8 | 78 | 3080 | 3100 | A | A | 11.5 | 10.1 |

As shown in Table 4, the cured body obtained by curing the paste of Example 1 had both of high flexural strength of 80 [MPa] and breaking energy of 95 [N·mm], and had high strength and toughness. In addition, the paste of Example 1 exhibited good paste operability in that it slightly adhered to the gloves, but once adhered to the denture base and gypsum, the paste could easily peel off from the gloves. Additionally, the paste hardness and the paste property after one month also hardly changed from those immediately after the preparation, and the storage stability was also excellent. Further, the paste of Example 1 could be firmly adhered to an adherend using an adhesive and was also excellent in adhesive durability.

Examples 2 to 23

Evaluation was performed in the same manner as in Example 1, except that the composition of the paste was changed as shown in Table 2 and the composition of the adhesive was changed as shown in Table 3. Results are indicated in Table 4. As indicated in Table 4, all of the cured bodies obtained by curing the pastes of Examples 2 to 23 had high strength and toughness. In addition, the pastes of Examples 2 to 23 were also excellent in the paste operability and storage stability. Further, the pastes of Examples 2 to 23 could be firmly adhered to an adherend using an adhesive, and also had excellent adhesive durability.

Comparative Examples 1 to 3

Evaluation was performed in the same manner as in Example 1, except that the filler used was changed from the monomer-absorbing porous organic crosslinked polymer (B) to the fillers indicated in Table 5, and the composition of the adhesives was changed as indicated in Table 6. The amount of each component in Table 5 and Table 6 is in parts by mass. Results are shown in Table 7.

TABLE 5

| Comparative Example No. | (A) (Meth)acrylic monomer Type | Amount | Type | Amount | Filler Type | Amount | (C) Polymerization initiator Type | Amount | Type | Amount | (D) (Meth)acrylic non-crosslinked polymer Type | Amount |
|---|---|---|---|---|---|---|---|---|---|---|---|---|
| Comparative Example 1 | HPr | 50 | ND | 50 | PMMA-X | 160 | CQ | 0.5 | DMBE | 0.5 | PEMA | 25 |
| Comparative Example 2 | HPr | 50 | ND | 50 | AC-X | 80 | CQ | 0.5 | DMBE | 0.5 | PEMA | 25 |
| Comparative Example 3 | HPr | 50 | ND | 50 | Silica | 400 | CQ | 0.5 | DMBE | 0.5 | PEMA | 25 |

TABLE 6

| Comparative Example No. | (a) (Meth)acrylic non-crosslinked polymer Type | Amount | (b) (Meth)acrylic monomer Type | Amount | (c) Organic solvent Type | Amount | Type | Amount | (d) Polymerization initiator Type | Amount |
|---|---|---|---|---|---|---|---|---|---|---|
| Comparative Example 1 | P (EMA-MMA) | 5.0 | TMMT | 5.0 | Ethyl acetate | 50.0 | Acetone | 50.0 | — | — |
| Comparative Example 2 | P (EMA-MMA) | 5.0 | TMMT | 5.0 | Ethyl acetate | 50.0 | Acetone | 50.0 | — | — |
| Comparative Example 3 | P (EMA-MMA) | 5.0 | TMMT | 5.0 | Ethyl acetate | 50.0 | Acetone | 50.0 | — | — |

TABLE 7

| Comparative Example No. | Monomer absorption amount [g/g] | Amount of (B) × absorption amount | Flexural strength [Mpa] | Modulus of elasticity [GPa] | Breaking energy [N · mm] | Paste hardness [g] Initial | One month later | Paste adhesiveness | Paste property one month later | Bond strength [MPa] Initial | After durability test |
|---|---|---|---|---|---|---|---|---|---|---|---|
| Comparative Example 1 | 0.5 | 85 | 39 | 1.5 | 15 | 1350 | 8230 | B | C | 4.2 | 2.1 |
| Comparative Example 2 | 1.3 | 101 | 26 | 0.2 | 55 | 1620 | 3250 | B | B | 3.9 | 1.9 |
| Comparative Example 3 | — | — | 96 | 8.5 | 19 | 690 | 760 | C | B | 3.5 | 1.8 |

As shown in Table 7, the cured bodies obtained from the pastes of Comparative Examples 1 and 2 in which the non-porous organic crosslinked polymer (B') was formulated as a filler instead of the monomer-absorbing porous organic crosslinked polymer (B) had low strength and toughness and inferior storage stability. In addition, the pastes of Comparative Examples 1 and 2 had low adhesiveness when adhered to an adherend using the adhesive, and also had inferior adhesiveness durability. In addition, in the paste of Comparative Example 3 in which silica was formulated as a filler instead of the monomer-absorbing porous organic crosslinked polymer (B) had high strength, but low toughness and inferior operability. In addition, the paste of Comparative Example 3 had low adhesiveness when adhered to an adherend using the adhesive and was also inferior in adhesive durability.

The invention claimed is:
1. A denture base curable composition in a paste state, comprising:
(A) a (meth)acrylic monomer,
(B) a monomer-absorbing porous organic crosslinked polymer capable of absorbing the (meth)acrylic monomer (A), and
(C) a polymerization initiator selected from a photo-polymerization initiator and a thermal polymerization initiator,
wherein a content of the monomer-absorbing porous organic crosslinked polymer (B) is 20 to 80 parts by mass per 100 parts by mass of the (meth)acrylic monomer (A), and
wherein an absorption amount $R_{Ab}$ representing an amount of the (meth)acrylic monomer (A) absorbed per unit amount of the monomer-absorbing porous organic crosslinked polymer (B) is 1.5 or more, with $R_{Ab}$ being defined by the following equation:

$$R_{Ab}=\{(g\text{-}A)/(g\text{-}B)\},$$

wherein g-A (unit: g) represents an amount of the (meth)acrylic monomer (A) absorbed by the monomer-absorbing porous organic crosslinked polymer (B) in an amount of g-B (unit: g), and $R_{Ab}$ being measured according to JIS K5101-13-1:2004, and
wherein a product obtained by multiplying the content (unit: g) of the monomer-absorbing porous organic crosslinked polymer (B) per unit amount (unit: g) of the (meth)acrylic monomer (A) by the absorption amount $R_{Ab}$ is 0.65 to 1.65.

2. The denture base curable composition according to claim 1, further comprising (D) a (meth)acrylic non-crosslinked polymer, wherein the content of the (meth)acrylic non-crosslinked polymer (D) is 5 to 40 parts by mass per 100 parts by mass of the (meth)acrylic monomer (A).

3. The denture base curable composition according to claim 1, wherein a content of (B') a non-porous organic crosslinked polymer is less than 10 parts by mass per 100 parts by mass of the (meth)acrylic monomer (A).

4. A kit, comprising:
    the denture base curable composition according to claim 1 as a denture base hard relining material or a denture base repairing resin, and
    a liquid adhesive: comprising (a) (meth)acrylic non-crosslinked polymer, (b) a (meth)acrylic monomer, and (c) an organic solvent,
    wherein the liquid adhesive is used for bonding to the denture base.

5. The kit according to claim 4, wherein the liquid adhesive further comprises (d) a polymerization initiator.

6. A denture base, comprising a cured body of the denture base curable composition according to claim 1.

7. A plate denture comprising the denture base according to claim 6 and an artificial tooth fixed to the denture base.

\* \* \* \* \*